United States Patent

Visser et al.

[11] Patent Number: 5,080,896
[45] Date of Patent: Jan. 14, 1992

[54] SYNTHETIC IMMUNOGEN

[75] Inventors: Nicolaas Visser, Boxmeer; Petrus J. Boon, Oss, both of Netherlands

[73] Assignee: Akzo N. V., Arnhem, Netherlands

[21] Appl. No.: 191,801

[22] Filed: May 6, 1988

Related U.S. Application Data

[63] Continuation of Ser. No. 829,760, Feb. 14, 1986, abandoned.

[30] Foreign Application Priority Data

Feb. 14, 1985 [NL] Netherlands ............................ 8500411

[51] Int. Cl.$^5$ .................... A61K 39/02; A61K 39/12; A61K 37/24; C07K 17/00
[52] U.S. Cl. .......................................... 424/88; 424/89; 424/90; 424/91; 424/92; 424/450; 424/460; 424/468; 530/322; 530/330; 530/403; 530/404; 530/405; 530/406
[58] Field of Search ............... 424/88, 89, 90, 91, 424/92, 460, 468, 450; 436/829; 530/330, 322, 403, 404, 405, 406

[56] References Cited

U.S. PATENT DOCUMENTS

| | | | |
|---|---|---|---|
| 4,432,969 | 2/1984 | Batchelor | 424/91 |
| 4,517,304 | 5/1985 | Stott et al. | 424/518 |
| 4,578,269 | 3/1986 | Morein | 424/88 |
| 4,803,070 | 2/1989 | Cantrell et al. | 424/92 |
| 4,806,350 | 2/1989 | Gerber | 424/88 |
| 4,806,352 | 2/1989 | Cantrell | 424/92 |

FOREIGN PATENT DOCUMENTS 0244719 11/1987 European Pat. Off.

OTHER PUBLICATIONS

Morein et al., (1984) Nature 308:457–460.
Nourath et al., (1984) J. Gen. Virol. 65:1009–1014.
Hopp (1984) Mol. Immunol. 21:13–16.

*Primary Examiner*—Jefrey E. Russel
*Assistant Examiner*—Kay Kim
*Attorney, Agent, or Firm*—William M. Blackstone

[57] ABSTRACT

The present invention concerns novel immunogens. These immunogens comprise novel compounds which consist of an antigen or antigenic determinant couple dot an amphiphilic adjuvant molecule and optionally also free amphiphilic adjuvant molecules. An advantageous features of these novel immunogens is the presence of both an excellent immunogen activity as well as a pronounced adjuvant activity in a single complex.

50 Claims, No Drawings

SYNTHETIC IMMUNOGEN

This is a continuing application of application Ser. No. 06/829,760 filed Feb. 14, 1986, now abandoned.

The invention relates to an immunogen consisting of at least one type of antigen or antigenic determinant coupled to a carrier; to a compound comprising an amphiphilic adjuvant; to methods for the preparation of, respectively, the immunogen and the compound comprising the amphiphilic adjuvant; as well as to pharmaceutical preparations possessing immunizing activity and containing such an immunogen.

In man and animals, an immune response can be brought about by inoculating them with non-autologous antigens. This is utilized, in particular, in protecting man and animals against infections by pathogenic organisms such as viruses, bacteria, parasites and the like, but also in stimulating the production of antibodies against non-pathogenic substances, for example for the production of antisera for use in diagnostic tests, and for immunological sterilization or castration.

In general, such an active immunization is carried out by inoculating the human object or animal to be protected with inactivated or attenuated strains of the pathogenic organisms.

A disadvantage of inoculation with inactivated material is that the immunizing power is often low, as a consequence of the partial denaturation of the antigens which occurs during inactivation. Inoculation with attenuated strains entails the risk that the strains still possess a certain pathogenicity or that they become pathogenic again through spontaneous mutation.

Hence, better alternatives are increasingly being sought. Inter alia, use is made, in this context, of immunogens which consist of antigens or antigenic determinants which are coupled to a carrier. In this way, even antigens or antigenic determinants which do not per se bring about an immune response can be made active as an immunogen.

The numerous types of carriers which are used for this purpose have, in general, disadvantages which stand in the way of a general use, for example in man, such as toxicity and possible cross-reaction with endogenous substances.

It is an object of the present invention to overcome such disadvantages.

An immunogen according to the invention is characterized in that it consists in the main of a micelle of at least one type of amphiphilic adjuvant and that the antigens and/or the antigenic determinants are covalently coupled to at least a part of these amphiphilic adjuvants.

The antigen and/or antigenic determinants in the immunogen according to the invention can, for example, be polypeptides, proteins, protein fragments, oligosaccharides or polysaccharides, oligonucleotides or polynucleotides or other antigenic compounds. For example, these may be derived from pathogenic organisms such as viruses, bacteria, parasites or the like, and may optionally comprise a fragment of an antigen originating from these organisms, or they may be prepared synthetically and correspond to natural antigens or antigenic determinants, or may be derived from these. The immunogens according to the invention can also comprise antigens or antigenic determinants which correspond to, for example, hormones or to hormone analogues or to particular drugs etc. Furthermore the antigen also may be an anti-idiotype antibody or a suitable fragment thereof. Such an anti-idiotype mimics an antigen or antigenic determinant as to its relevant immunogenic property.

The antigens and antigenic determinants can be isolated from biological or microbiological preparations and can thereafter be purified, if desired. They can, where appropriate, be obtained by splitting or fragmentation of larger molecules which are isolated from the above mentioned preparations.

Furthermore, the antigens and antigenic determinants of low molecular weight, in particular, can advantageously be prepared by chemical synthesis. For example, this is very readily possible with small polypeptides, oligonucleotides and oligosaccharides.

Such small, but in particular also larger, antigenic molecules can also be advantageously prepared with the aid of cell cultures or cultures of micro-organisms which contain a recombinant DNA which codes for the production of the particular molecule. It is also possible, with the aid of recombinant DNA techniques, to prepare antigenic molecules which, for example, contain a plurality of antigenic determinants which occur on different antigens which, for example, are derived from different pathogens or from variants of one and the same pathogen.

By an antigenic determinant there is understood, in this context, a chemical structure which can form a recognition site for one or more types of antibodies directed against this recognition site. In this sense, an antigenic determinant can comprise one or more epitopes. By an antigenic determinant there is also understood a so-called hapten—an independently occurring chemical entity which, for example as a result of its relatively small dimensions, is capable of functioning as an immunogen unless it is bound to a carrier.

Specific examples of suitable amphiphilic adjuvants for use in the immunogens according to the invention are avridine (N,N-dioctadecyl-N',N'-bis(2-hydroxyethyl)-propanediamine), the lipoidal amine 4-aminomethyl-1-(2,3-(di-n-decyloxy)-n-propyl)-4-phenylpiperidine, dimethyl-dioctadecylammonium bromide, lauryl-muramyl-dipeptide, lauryltetrapeptide ($N^2$-[N-(N-lauryl-L-alanyl)-$\gamma$-D-glutamyl]-$N^6$-(glycyl)-D,D-L,L-2,6-diaminepimelamic acid, L-tyrosine and alkyl derivatives thereof, maltose tetrapalmitate, pluronic polyols, L-tyrosine-azobenzene-p-arsonate, sorbitanmonooleate (Span 80), trehalose derivatives (such as trehalose dimycolate), retinoic acid and derivatives thereof, D,L-$\alpha$-tocopherol (vitamin E), lipid A and analogues glyco-$\alpha$-sides such as, for example, saponins (for instance) Quil A from the bark of Quillaja saponaria Molina) and carbomers, such as Carbopol 934 ®, Carbopol 940 ® and Carbopol 941 ® and copolymers of hydrofobic and hydrophylic phenyl-derivatives.

The immunogen according to the invention comprises the molecular compound as described above, or a multitude of these molecules associated in e.g. micellar complexes, which can have various forms and/or dimensions.

These micelles can be formed by interaction between identical amphiphilic adjuvants or by interaction between two or more types of different amphiphilic adjuvants.

In the immunogen according to the invention, the antigens and/or antigenic determinants are covalently coupled to at least a part of the amphiphilic adjuvants.

The nature of this coupling depends on the groups involved in this coupling, on, respectively, the amphiphilic adjuvants and the antigens and/or antigenic determinants, and on the nature of the particular reactive component itself. This coupling can be directly between the groups of, respectively, an antigen or antigenic determinant and the adjuvant molecule indirectly through the presence of a so-called "linker" between the antigen and the antigenic determinant and the adjuvant molecule.

An immunogen according to the present invention can consist of a micelle to which one type of antigen or antigenic determinant is coupled or of a micelle to which at least two different types of antigen and/or antigenic determinant are coupled. In this last case, the different types can be characteristic of a particular pathogen or of a substance against which immunization is desired or, if required, different variants thereof, or of different unrelated types of pathogens and/or other substances against which immunization is desired.

The immunogen according to the invention can, if desired, be stabilized. Such stabilization can for example be achieved by at least a portion of the antigens and/or antigenic determinants and/or at least a portion of amphiphilic adjuvants being linked to one another. Moreover, for stabilization the immunogen, which may or may not be linked, can be used in an encapsulated form. Suitable capsules are, for example, those which are composed of polymers which can decompose in the body, such as polylactic acid, polyglycolic acid, mixed polymers of lactic acid and glycolic acid, polyamino acid, mixed polymers of lactic acid and one or more amino acids, or polymerized albumin.

A number of alternative methods are available for the preparation of an immunogen according to the invention.

For example, it is possible to start from compounds of at least one antigen and/or antigenic determinant with at least one amphiphilic adjuvant. The antigen and/or antigenic determinant, on the one hand, and amphiphilic adjuvant on the other, can if desired be joined together by one or more linkers. Such derivatives of amphiphilic adjuvants also form part of the invention.

An immunogen according to the invention can be prepared from the above mentioned compounds by forming a micelle therefrom in a manner customary for compounds of this type, and thereafter isolating the immunogen. For this, it is possible to start from one type of compound which comprises at least one antigen and/or antigenic determinant and at least one amphiphile, bu tit is also possible to prepare an immunogen from a mixture of compounds with at least two different antigens and/or antigenic determinants.

Preferably, the said micelles are prepared by ultrasonication of a solution which contains the above mentioned derivatives of amphiphilic adjuvants in a quantity equal to at least the critical micellar concentration. If desired, the amphiphilic adjuvants can be mixed with corresponding or different free amphiphilic adjuvants, and immunogens with mixed micelles, partially consisting of unbound adjuvant molecules, can be prepared therefrom.

Another method for the preparation of an immunogen according to the invention is based on the covalent coupling of antigens and/or antigenic determinants in a manner customary per se for such coupling reactions, to a micelle which consists in the main of amphiphilic adjuvants, after which the immunogen is isolated. This coupling takes place through the reaction of reactive groups on the adjuvant micelle with reactive groups of the antigens and/or antigenic determinants.

If desired, the amphiphilic adjuvants, antigens and/or antigenic determinants can be provided with linkers which contain reactive groups.

Example of suitable reactive groups are amine groups, carboxyl groups, hydroxyl groups, thiol groups, disulphide groups, carbonyl groups, maleimide groups and activated carboxyl groups.

Regardless of the method of preparation, the immunogen can, if desired, also be stabilized (for example by mutual linking of the adjuvant molecules, antigens and/or antigenic determinants) and/or be protected against hydrolytic digestion (for example by encapsulating the immunogen, which may or may not be linked, in, for example, a polymer which can be decomposed in the body).

The mutual linking of the adjuvants, antigenic determinants and/or amphiphilic adjuvants can be carried out with any reagent possessing at least two reactive groups which are suitable for reacting with the components to be linked. For the linking of polypeptides use is advantageously made, for example, of glutaraldehyde or formaldehyde, or of bifunctional reagents, such as homobifunctional reagents (bisamidates or bisuccinimidyl esters or heterobifunctional reagents (for example compounds which possess an azidophenyl group and a maleimido, amidate, succinimidyl, haloketone or activated fluorobenzene group).

Examples of polymeric materials which can be digested in the body and which are suitable for the encapsulation of the immunogen have already been mentioned above. Such materials can be applied onto or around the immunogen in a manner customary for this purpose.

The immunogen according to the invention is in particular suitable for use in vaccines.

Such a vaccine can inter alia be used for immunizing man or animals against certain pathogens (viruses, bacteria, parasites and the like) or allergens, for so-called "priming" (wherein the body is not directly stimulated to form specific free antibodies but in fact is preconditioned so that after subsequent infection or revaccination a powerful immunizing reaction is elicited), or, for example, for immunological sterilization or castration (wherein antibodies directed against substances vital for the reproductive processes, such as certain hormones, are caused to be produced).

The above mentioned vaccines can, if desired, comprise two or more different antigens and/or antigenic determinants which, for example, are coupled to one and the same micelle, or can comprise a mixture of two or more immunogens according to the invention, each of which itself comprises a certain type of antigen or antigenic determinant. The different antigens and/or antigenic determinants can be representative of different pathogens etc., or of variants of one and the same pathogen, etc.

In order to be able to use an immunogen according to the invention for vaccination purposes the immunogen must be converted to a form suitable for the particular pharmaceutical administration. For intramuscular or subcutaneous administration the immunogen must be mixed with a suitable liquid, for example a physiological salt solution.

For intranasal or intra-ocular administration, for example in the form of a spray, an aqueous medium is also the most suitable. For local, for example oral, administration it will in many cases be necessary to use an administration form wherein the immunogen is temporarily protected, for example against saccharolytic enzymes present in the oral cavity, or against proteolytic enzymes present in the stomach, or against detergents.

Such protection can be achieved, for example, by encapsulating together one or more immunogens according to the invention in a suitable material, by incorporating the immunogen in a delayed-release and/or controlled-release administration form, or by chemically modifying, in polypeptide antigens and/or antigenic determinants, sites which are sensitive to proteolytic enzymes, in such a way that proteolytic cleavage is impossible or is greatly hindered.

EXAMPLE 1

Preparation of Thiolated Quil A

A. Via Reduction Amination 45 mg of Quil A, purified beforehand on DEAE-Sephacel according to K. Dalsgaard ("Saponin Adjuvants" Archiv Fuer die gesamte Virusforschung 44, 243-254 (1974)) are dissolved in 0.8 ml of 0.1 mol/l sodium phosphate buffer of pH 8.0. The clear solution is diluted with 1.5 ml of methanol and then mixed with a solution of 60 mg of 2-(2-pyridyldithio)-ethylamine.HCl in 0.2 ml of the said phosphate buffer. 0.05 ml of a 1 mol/l solution of sodium cyanoborohydride in methanol is added, after which the reaction mixture is stirred for 20 hours at room temperature. After addition of 0.05 ml of acetic acid, the low molecular components are removed by gel filtration through Sephadex G-25 in 0.1 mol/l sodium phosphate buffer of pH 6.0, containing 5 mmol/l EDTA.

Thereafter, dithioerythritol is added, until the concentration is 20 mmol/l, to the fraction containing Quil A. After 20 minutes at room temperature, the thiolated Quil A is isolated by gel filtration through Sephadex G-25 in the said phosphate/EDTA buffer.

B. Via Amidation 10 mg of purified Quil A is dissolved in 0.2 ml of water and 0.2 ml of dimethylformamide. The pH of the solution is brought to 3-3.5 with 1 mol/l HCl, after which 6.0 mg of 1-ethyl-3-(3-dimethylaminopropyl)-carbodiimide.HCl are added, with stirring. After 3 minutes at room temperature, 7.0 mg of 2-(2-pyridyldithio)-ethylamine.HCl in 0.2 ml of 0.2 mol/l sodium phosphate buffer of pH 8.0 are added. The pH of the solution is brought to 8 by adding ethyldiisopropylamine. After 30 minutes, acetic acid is added until the pH is 5-6, after which the derivatised Quil A is isolated by gel filtration through Sephadex G-25 in 0.1 mol/l sodium buffer of pH 6.0, containing 5 mmol/l EDTA.

The reduction with dithioerythritol and the isolation of thiolated Quil A are carried out as described under A.

C. Via Activation with 2,2,2-trifluoroethanesulphonylchloride 50 mg of Quil A, purified as described under A, are dissolved in dry pyridine, after which the solution is evaporated in vacuo. This procedure is repeated once. The Quil A thus obtained is subsequently suspended in dry dioxane (0.5 ml), after which 8 μl of 2,2,2-trifluoroethanesulphonyl chloride are added with vigorous mixing. After having been stirred for 10 minutes at room temperature, the mixture is diluted with 5 ml of 0.05 mol/l HCl, which has beforehand been cooled to 4° C., and is then dialysed for 5 hours against 0.01 mol/l HCl (2×1 liter) at 4° C.

A solution of 40 mg of 2-(2-pyridyldithio)-ethylamine.HCl in 1 ml of 0.5 mol/l sodium phosphate buffer of pH 8.0 is added to the resulting solution of Quil A at 4° C. The pH is brought to 8.0 by adding NaOH, after which the mixture is stirred for 18 hours at 4° C. The derivatised Quil A is isolated by gel filtration through Sephadex G-25 in 0.2 mol/l phosphate buffer of pH 6.0 containing 5 mmol/l EDTA.

The reduction with dithioerythritol and isolation of the thiolated Quil A are carried our as described under A.

EXAMPLE 2

β-endorphin-(6-17)-immunogen.I

A. Preparation of Activated Avridine 1.67 g (25 mmol) of N,N-dioctadecyl-N',N'-bis(2-hydroxyethyl)-propanediamine [avridine: CP 20961] are added to a solution of 2.82 g (10 mmol) of trifluoromethanesulphonic anhydride in 20 ml of methylene chloride. 0.4 ml (5.2 mmol) of pyridine is added, after which the mixture is stirred for 60 minutes at room temperature. A solution of 2.5 g (32 mmol) of thiolacetic acid in water, brought to pH 7.5 with NaOH, is then added. The two-phase system is stirred vigorously for 60 minutes. The methylene chloride layer is separated off, dried over MgSO$_4$ and evaporated. The residue is recrystallized from methylene chloride/ether.

The S-acetyl derivative of avridine, in methylene chloride, is mixed with avridine (1:1). The solvent is evaporated off and the residue is dispersed (5 mg/ml) in 0.1 mol/l sodium phosphate buffer of pH 7.0, containing 0.1 mol/l NaCl and 0.05 mol/l EDTA. The dispersion is ultrasonicated under N$_2$ for 5 minutes at 60° C. [Branson Sonifier; microtip, 20 W].

B. Preparation of β-endorphin-(6-17)-immunogen

Deoxygenated 0.5 mol/l hydroxylamine of pH 7.2 is added, to a final concentration of 0.04 mol/l, to a solution of derivatised avridine prepared according to Example A. The mixture is kept for 30 minutes at 35+ C. in an N$_2$ atmosphere. Thereafter there is added, at 20° C., a solution of 1.5 equivalents, relative to the thiolated avridine, of a maleimide derivative of β-endorphin-(6-17)

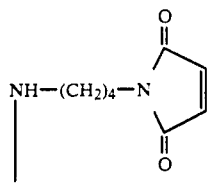

H—Thr—Ser—Glu—Lys—Ser—Glu—Thr—Pro—Leu—Val—Thr—Leu—OH, dissolved in 0.1 mol/l sodium phosphate buffer of pH 6.0, containing 0.005 mol/l EDTA.

The mixture is stirred for 15 hours under $N_2$ and then dialysed against an 0.05 mol/l sodium phosphate buffer of pH 7.4, which contains 0.1 mol/l NaCl.

EXAMPLE 3

β-endorphin-(6-17)-immunogen. II

To a solution of thiolated Quil A (7 mg/ml), prepared according to 1A, are added 1.2 mole-equivalents (based on the thiol groups) of a maleimide derivative of β-endorphin-(6-17), namely

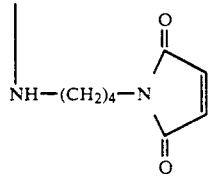

H—Thr—Ser—Glu—Lys—Ser—Glu—Thr—Pro—Leu—Val—Thr—Leu—OH in 0.01 mol/l phosphate buffer of pH 6.0, containing 5 mmol/l EDTA.

This mixture is allowed to react to react for 1 hour at room temperature and thereafter is dialysed for 15 hours at 0° C. against 0.02 mol/l sodium phosphate buffer of pH 7.4, which contains 150 mmol/ml NaCl.

EXAMPLE 4

Parvovirus Immunogen

A. Preparation of Porcine Parvovirus Antigen

A 65 kD coat protein of porcine parvovirus (PPV) is isolated in accordance with the procedure described by Molitor, T. W., Joo, H. S. and Collet, M. S.: J. Virology 45, 842-854 (1983):

a concentrated $CaCl_2$ solution is added to a PPV-containing tissue culture supernatant until the $CaCl_2$ concentration is 25 mmol/l;

the virus precipitate thereby formed is centrifuged for 20 minutes at 12,000 xg;

the virus-containing pellet is then centrifuged in a CsCl gradient;

The fraction of density 1.3 g/ml is isolated, dialysed and then treated for 3 minutes with 1% sodium dodecyl sulphate (SDS); and the 65 kD protein is isolated by SDS/PAGE fractionation, dialysed and freeze-dried.

B. Derivatisation of Porcine Parvovirus Antigen

The protein obtained under A. is dissolved in 0.1 mol/l sodium phosphate buffer of pH 7.5 to a concentration of 3 mg/ml, and is then treated with 5 mole-equivalents of N-succinimidyl-4-(N-maleimidomethyl)-cyclohexane-1-carboxylate (SMCC) for 30 minutes at room temperature.

The excess SMCC is removed by gel filtration through Sephadex G-25 in 0.1 mol/l sodium phosphate buffer of pH 6.0, which contains 0.9% NaCl and 5 mmol/l EDTA.

C. Preparation of Immunogen

The derivatised PPV coat protein obtained by B. is mixed with thiolated Quil A, prepared according to Example 1A, in a ratio of 1:4 (Quil A:protein) (weight/weight).

The solution is kept for 5 hours at room temperature after which the immunogen is isolated by centrifuging it in a 10-40% (weight/weight) sucrose gradient at 250,000 xg for 10 hours at +4° C.

The PPV immunogen is subsequently dialysed against 0.02 mol/l phosphate buffer of pH 7.4, which contains 150 mmol.l NaCl.

EXAMPLE 5

Parvovirus Peptide Immunogen

The maleimide derivative of the peptide:

H—Asn—Leu—Ala—Lys—Lys—Lys—Ala—Lys—Gly—Thr—

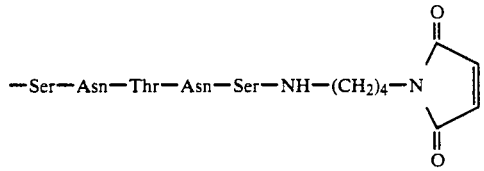

—Ser—Asn—Thr—Asn—Ser—NH—(CH₂)₄—N (obtained from AMGen), which corresponds to a part sequence of a PPV coat protein, is coupled, in the manner described under Example 3, to thiolated Quil A.

EXAMPLE 4

HBsAg Immunogen

A polypeptide derived from HBsAg (hepatitis B surface antigen), wherein the amino-terminal hydrophobic portion is absent, is prepared according to a method described by Fujisawa et al. (Nucleic Acids Research 11 3581-3590 (1983)) in *E. coli*. After extracting from these bacteria, the polypeptide is purified by means of affinity chromatography.

The purified HBsAg derivative is activated, before the coupling to adjuvant, by means of SMCC as described under Example 4B.

The activated polypeptide is subsequently coupled to thiolated Quil A analogously to the method described under Example 4C.

EXAMPLE 7

Parvovirus Immunogen

A. Preparation of Thiolated Quil A

Quil A (20 mg) is dissolved in dimethylformamide (0.5 ml). Following the addition of HCl (10 μmoles; 1 N solution in DMF) and cooling of the solution at 0° C., carbonylidiimidazole (20 μmoles in 0.04 ml DMF) is added. The reaction mixture is stirred at 0° C. for 30 minutes. 2-(2-pyridyldithio)-ethylamine.Hcl (50 μmoles) and ethyldiisopropylamine (50 μmoles) are then added. The resulting clear solution is kept at room temperature for 18 hours. DMF is removed by rotary evaporation in vacuo and the resulting syrup is then dissolved in water (2 ml). Derivatized Quil A is isolated by gel filtration on Sephadex G-25 in 0.1 mol/l sodium-phosphate, pH 6.0, also containing 5 mmol/l EDTA. Thiolated Quil A is obtained following reduction with dithioerythritol and gel filtration on Sephadex G-25 as described under Example 1A.

B. Preparation of Derivatized Porcine-Parvovirus antigen

A solution of the parvovirus protein (2 mg), isolated as described under Example 4A, in 0.1 mol/l sodium-phosphate, pH 7.6, is treated with N-succinimidyl 3-(2-pyridyldithio)-propionate (SPDP; 3.2 μmoles in 0.3 ml ethanol) for 3 hours at room temperature. The 2-pyridyldisulfide substituted protein is isolated by gel filtration on Sephadex G-25 in 0.1 mol/l sodiumphosphate, pH 6.0, also containing 5 mmol/l EDTA.

C. Preparation of the Immunogen

A solution of thiolated Quil A (containing 0.6 μmol of free thiol groups), obtained as described under A, is added to a solution of 2-pyridyldisulfide-substituted porcine parvovirus protein (containing 0.45 μmoles at 2-pyridyldisulfide groups), obtained as described under B.

The coupling reaction, which is monitored by measuring the release of pyridine-2-thion, is completed within 2 hours., The quil A-protein conjugate is subsequently dialysed against 0.02 mol/l sodiumphosphate, pH 7.4, also containing 150 mmol/l NaCl.

EXAMPLE 8

Efficacy of Immunogen

Two groups of 10 six weeks old Swiss albino mice were repeatedly inoculated i.p. with a rabies virus coat-peptide coupled to either KLH or Quil A.

This peptide has the amino acid sequence Asp-Tyr-Arg-Trp-Leu-Arg-Thr-Val-Lys-Thr-Thr-Lys-Gly-Ser. Doses of 50 μg of the above peptide bonded either to 50 μg of Quil A or to 500 μg of KLH were repeatedly inoculated in each of the mice.

Sera from these mice, diluted 1/80, were tested by enzyme-labeled immunosorbent assay (ELISA) after the third and the fourth inoculation using the following respective test systems:

After third inoculation: virus-coated micro-titration plates—mouse serum—anti—mouse Ig-HRP-conjugate after fourth inoculation: micro-titration plates coated with human anti-rabies monoclonal antibodies—ERA-virus antigen—mouse serum—anti-mouse-Ig-HRP-conjugate.

The results are summarized in the following table.

| serum from mice inoculated with | Response (at 450 nm) after | |
|---|---|---|
| | 3rd inoculation | 4th inoculation |
| KLH-peptide | 0.185 | 0.939 |
| Quil-A peptide | 0.200 | 0.997 |
| control serum | 0.072 | 0.240 |

The above results indicated that antibodies raised against the Quil A-peptide complex show excellent virus binding—at least as good as the virus binding by antibodies raised against KLH-peptide complexes.

EXAMPLE 9

Adjuvant Effect of Saponine Derivatives

Four groups of 10 nine weeks old Swiss albino mice were i.m. inoculated with Pseudorables (PR) antigen as such or together with the adjuvant to be tester.

After 3, 9 and 15 weeks sera were collected and pooled to be tested as to anti-PR response in an enzyme-linked immunosorbent assay (ELISA).

The results are summarized in the following table.

TABLE

| Adjuvant | ELISA ($^2$log titer: end point dilution) after (weeks) | | |
|---|---|---|---|
| | 3 | 9 | 15 |
| no adjuvant (in saline) | 9.4 | 10.6 | 9.9 |
| Quil A (batch no. L-77.26) | 11.4 | 12.4 | 12.0 |
| activated Quil A according to Example 7A) | 11.4 | 12.2 | 11.8 |
| peptide-coupled Quil A (according to Example 7C) | 11.5 | 12.1 | 11.6 |

The above results indicate that the adjuvant activity of Quil A remains intact after derivatizing the adjuvant, and even after coupling of the peptide.

EXAMPLE 10

Preparation of 2-pyridyl-disulfide Containing Adjuvant Derivatives

A. Pluronic ® polyols

The Pluronic ® polyols is a series of related difunctional block-polymers, built up from polyoxypropylene and polyoxyethylene, terminating in primary hydroxyl groups. In the related R-series the polyols contain terminal secondary hydroxyl groups. These polyols are surface active agents manufactured by BASF Wyandotte. Several members of the polyol series are recognized as effective adjuvants, like the Pluronics ® L101, L121, 25R1 and 31R1.

Said Pluronics are derivatized at their terminal hydroxyl groups. Residual water is removed from the polyols by filtration through a column of basic aluminiumoxide using chloroform-methanol (9:1; v/v) as the solvent and eluent. Alkylation at the hydroxyl groups is effected by reacting the respective alcoholates, which are prepared in tetrahydrofuran solution using naphtyl-sodium, with ethyl 2-bromo-acetate. The resulting ethyl esters are isolated by chromatography on silica. Analysis by nmr spectroscopy of samples that are exhaustively acetylated using acetic anhydride, reveals that alkylation proceeds at more than 80% of available hydroxyl groups. Ethyl ester derivatives are quantitatively saponified with potassium hydroxide in aqueous methanol. Resulting free acid derivatives are reacted in dichloromethane solution with 2-(2-pyridyldithio)-ethylamine following in situ activation of the carboxylic acid functions with 1-ethyl-3(3-dimethylaminopropyl)carbodiimide in the presence of N-hydroxybenzotriazole. The 2-pyridyl-disulfide substituted Pluronic derivatives contain 1.2-1.5 moles of pyridyldisulfide per mole.

B. Tetronic ® polyols

The Tetronic ® polyols is a tetrafunctional series of high molecular weight block polymers (BASF Wyandotte), obtained by alkoxylating a diamine.

Tetronics 1301, 1501, 130R1 and 130R2 are derivatised at their four primary or secondary (R-series) hydroxyl functions as is described for the Pluronic polyols under A. The 2-pyridyldisulfide substituted Tetronic derivatives contained 1.8–2.0 moles of pyridyldisulfide per mole.

C. Carbopol ® resins

The Carbopol resins (carbomers) is a series of water soluble acrylic acid polymers, the members of which differ in molecular weight (450,000–4,000,000). To a solution of carbomer-907 (75 mg) in water (15 ml) is added 2-(2-pyridyldisulfide)-ethylamine hydrochloride (50 mg) and N-hydroxybenzotriazole (34 mg). The pH of the solution is brought to 6.2 by addition of N-ethylmorpholine, after which 1-ethyl-3-(3-dimethyl-aminopropyl)-carbodiimide hydrochloride (47.5 mg) is added. The reaction mixture is stirred at ambient temperature for 18 hours. The low molecular weight reactants are removed by dialysis for 5 days against several 2 liter changes of 0.1 mol/l sodiumphosphate pH 6.0, also containing 0.9% (w/w) sodium chloride and 5 mmol/l EDTA and 0.01% (w/w) sodium azide. The carbomer solution is then lyophilised to give a solid preparation with a carbomer content of 15% (w/w) and a content of 2-pyridyldisulfide groups of 0.20 μmol/mg.

Carbomer-910 is treated in an identical manner to give a preparation that contains 0.27 μmol of 2-pyridylsulfide groups per mg of the solid preparation.

D.

N,N-dioctadecyl,N'-(3-(2-pyridyldithio)-propionyl-1,3-propane diamine

Dioctadecylamine (0.29 g) and 3-(2-pyridylidithio)-propionic acid (0.11 g) are dissolved in dichloromethane (5 ml). The solution is cooled to 4° C., whereon N-hydroxybenzotriazole (0.05 g) and dicyclohexylcarbodiimide are successively added. The mixture is stirred for 1 hour at 4° C. and then for 18 hours at room temperature. The title compound (0.12 g) is obtained following chromatography of the reaction mixture on silica using toluene-ethanol (95:5; v/v) as the eluent. The disulfide bond in the title compound is quantitatively reduced when it is treated in dichloromethane-ethanol (1:1; v/v) solution with an excess of dithioerythritol, as is measured spectro-photometrically from the release of pyridine-2-thion.

EXAMPLE 11

*Pasteurella mutocida* Toxin Immunogens

A. Derivatisation of *Pasteurella multocida* Toxin (PMT)

PMT is isolated and purified as described by Foged, N. T., Pedersen, K. B. and Elling, F. FEMS Microbiology Letters 43, 45–51, 1987.

To a cooled solution (9.5 ml) of PMT (0.55 mg/ml) is added under stirring a solution (0.44 ml) of N-succinimidyl-3-(2-pyridyldithio)-propionate (SPDP from Pierce; 10 mg/ml) in ethanol. Following stirring at 4° C. for 1 hour, the pyridyldisulfide-substituted toxin is isolated by gelfiltration at 4° C. on a Sephadex G-50 column (70 ml) in a 0.04 mol/l sodiumphosphate buffer, pH 7.2, also containing 0.1 mol/l NaCl and 0.005 mol/l EDTA.

The PDP-toxin (19 ml; 0.27 mg/ml) is found to contain 7.8 moles of PDP-groups per mole of protein. To this PDP-toxin solution (7.0 ml) is added at 4° C. and under a nitrogen atmosphere a 0.2 mol/l solution of dithioerythritol (0.05 ml) in water. After 1 hr. at 4° C. the reduction is complete, as spectrophotometrically monitored by the release of pyridine-2-thion.

The excess reducing agent is removed by gelfiltration at 4° C. through Sephadex G-50 in 0.04 mol/l phosphate buffer of pH 7.2, which also contains 0.1 mol/l NaCl and 0.005 mol/l EDTA. The resulting thiolated PMT preparation (10 ml) is immediately used in the preparation of the immunogens described below.

B. PMT—Quil A Immunogen

A solution of pyridyldisulfide-substituted Quil A (0.40 ml, containing 0.68 μmol of pyridyldisulfide per ml), obtained as described under Example 7A, is added to a solution (10 ml) of the thiolated Pasteurella multocida toxin, obtained as described under A, at 4° C. The coupling reaction, which is monitored by measuring the release of pyridine-2-thion, is completed within 2 hours. The PMT-Quil A conjugate is subsequently dialysed at 4° C. against 0.04 mol/l sodium phosphate, pH 7.2, also containing 0.1 mol/l NaCl and 0.005 mol/l EDTA.

C. Pluronic ®— and Tetronic ®—PMT Immunogens

Pyridyldisulfide-substituted Pluronics 25R1 (0.4 mg) and 31R1 (0.4 mg), obtained as described under Example 10A, and the pyridyldisulfide-substituted Tretonic 1501 (0.8 mg) and 130R1 (1.0 mg), obtained as described under Example 10B, are each dissolved in ethanol (0.05 ml) and subsequently added to a separate sample (3.0 ml) of cold (4° C.) freshly prepared thiolated PMT solution, obtained as described under A. The mixtures are stirred at 4° C. for 18 hours and subsequently dialysed against 0.04 mol/l sodium phosphate pH 7.2, also containing 0.1 mol/l NaCl and 0.005 mol/l EDTA.

D. Avridine-like PMT Immunogen

A solution of N,N-dioctadecyl,N'-(3-(2-pyridyldithio)-propionyl)-1,3-propandiamine (0.15 mg; 0.2 μmoles), described under Example 10D, in ethanol (0.05 ml) is added at 4° C. to a freshly prepared solution (3.0 ml) of thiolated PMT, obtained as described under A. The mixture is kept at 4° C. for 18 hours and is then dialysed at 4° C. against 0.04 mol/l sodiumphosphate pH 7.4, also containing 0.1 mol/l sodiumchloride and 5 mmol/l EDTA.

E. Carbomer 910—PMT Immunogen

A solution of pyridyldisulfide-substituted carbomer 910 (3 mg), prepared as described under Example 10C, in water (0.5 ml), is added to a freshly prepared solution (6.0 ml) of thiolated PMT, obtained as described under A. The mixture is stirred for 6 hours and then dialysed against 0.04 mol/l sodiumphosphate buffer, pH 7.2, also containing 0.1 mol/l sodiumchloride and 5 mmol/l EDTA.

EXAMPLE 12

Parvoviras Peptide Immunogens

A. Preparation Of A Porcine Parvovirus Peptide

A procine parvovirus (ppv) 15-peptide derivative—

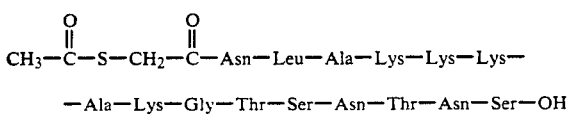

the sequence of which corresponds with a very hydrophilic region on a ppv coat protein VP1, is prepared by solid phase peptide synthesis on a VEGA Coupler 250 C automated synthesizer. The synthesis is started with 10 g of Fmoc-Ser(tBu)-p-alkoxybenzylalcohol resin (0.44 mmoles/g). Elongation to the tetrapeptide stage is performed by single couplings using 3 equivalents each of $N^\alpha$-Fmoc-protected amino acid (Fmoc=9-fluorenyl-methyloxycarbonyl), dicyclohexylcarbodiimide (DCC) and N-hydroxybenzotriazole (HOBt) in 6–7 ml of DMF per g resin. The side chains of Ser and Thr are protected by the t-butyloxycarbonyl (Boc)-group. After each synthesis cycle, the $N^\alpha$-Fmoc groups on the resin is removed by two successive treatments with 25% (v/v) piperidine in DMF for 2 min and 10 min, respectively.

The next eleven amino acids are coupled employing a protocol in which all couplings are carried out twice, using 2 equivalents each of Fmoc-amino acid, DCC and HOBt, for 4 hours and 2 hours, respectively. After each stage any unreacted sites are acylated by a treatment of the peptide-resin with pyridine-acetic acid-DMF (2:1:7, by vol.) for 30 min. The synthesis yields 15.4 g of the $N^\alpha$-Fmoc-15-peptide resin, that contains 0.20 mmoles of peptide/g resin, as determined spectrophotometrically (301 nm) measuring the amount of fluorine derivative formed when a sample of the $N^\alpha$-Fmoc-peptide resin is treated for 15 min. with 20% piperidine in DMF.

Part of the $N^\alpha$-Fmoc-peptide resin (5 g) is treated with piperidine-DMF (1:3; v/v) to remove the Fmoc group and is subsequently treated with 3 equivalent of N-succinimydyl-acetylthioacetate (SATA-ONSu). The resulting $N^\alpha$-SATA-peptide resin is then treated in TFA-dichloromethane (1:1; v/v) in order to release the peptide from the resin and to simultaneously remove the t-butyl-based protecting groups. The yield of $N^\alpha$-SATA-15-peptide is 1.75 g. An amino acid analysis of this peptide is in good agreement with the expected composition; Asp; 2.96; Ser, 1.87; Thr, 1.81; Gly, 1.04; Ala; 2.03; Leu, 1.01; Lys, 4.27.

B. PPV-peptide-Quil A Immunogen

A solution of pyridyldisulfide-substituted Quil A, (2.0 ml, containing 2.8 μmol pyridyldisulfide per ml), obtained as described under Example 7A, is added to a solution of the $N^\alpha$-SATA-peptide (4.2 μmol), obtained as described under A, in t-butanol-H₂O (2:1 v/v; 0.5 ml). To this mixture is added 0.2 mol/l hydroxylamine (0.28 ml) in water at pH 6.0. The reaction is monitored spectrophotometrically at 343 nm. After 3 hours the reaction is complete. The peptide-Quil A conjugate is purified by chromatography on a Sephadex G-50 column (80 ml) in 0.04 mol/l sodiumphoshate buffer, pH 7.4, also containing 0.1 mol/l NaCl and 0.005 mol/l EDTA. By this procedure the excess of peptide is removed completely. The resulting conjugate solution contains 1.9 mg Quil A/ml and 0.34 μmol peptide/ml.

C. Pluronic ® and Tetronic ® ppy-peptide Immunogens

Pyridyldisulfide-substituted Pluronic 25 $R_1$ (17 mg) and Pluronic 31 $R_1$ (10 mg), obtained as described under Example 10A, and the pyridyldisulfide-substituted Tetronics 1501 (20 mg) and Tetronic 130 $R_1$ (20 mg), obtained as described under Example 10B, are each dissolved in DMF (0.5 ml). To the four solutions is added a solution of the $N^\alpha$-SATA-15-peptide, described under A, in DMF (0.5 ml), containing 12, 8, 22, and 22 mg of the peptide respectively. To each of the four mixtures is added 0.5 mol/l hydroxylamine in water (0.05 ml). The mixtures are stirred for 20 hours at ambient temperature. Following dilution with water (4 ml), the preparations are dialysed against 0.04 mol/l sodium phosphate pH 6.0, also containing 0.001 mol/l EDTA. The resulting immunogens are then lyophilized.

D. Carbomer 910-ppy-peptide Immunogen

To a solution of pyridyldisulfide-substituted carbomer 910 (10 mg), described under Example 10C, in water (10 ml) is added a solution of the $N^\alpha$-SATA-15-peptide (7.5 mg), described under A, in t-butanol-H₂O (2:1, v/v; 1.5 ml). Then 0.2 mol/l hydroxylamine in water (1.0 ml) is added. The mixture is stirred for 6 hours at room temperature and then dialysed against 0.04 mol/l NaCl and 0.005 mol/l EDTA. The conjugate is isolated by lyophilisation.

We claim:

1. Compound containing an amphiphilic adjuvant molecule, comprising at least one amphiphilic glycoside and at least one antigen or antigenic determinant, which are covalently coupled to one another.

2. Compound according to claim 1, characterized in that the antigen or antigenic determinant and the amphiphilic adjuvant molecule are linked to one another by at least one linker.

3. Compound according to claim 1, comprising a saponin as the amphiphilic adjuvant.

4. Compound according to claim 2, characterized in that it contains a saponin as the amphiphilic adjuvant.

5. Immunogen comprising at least one type of antigens or antigenic determinants derived from a microorganism or a hormone coupled to a carrier, wherein the carrier is a micelle comprising at least one type of amphiphilic adjuvant molecules, of which at least a portion are covalently coupled to the antigens or antigenic determinants.

6. Immunogen according to claim 5, wherein the antigens or antigenic determinants are coupled to the amphiphilic adjuvant molecule by means of at least one linker.

7. Immunogen according to claim 5, comprising at least one saponin as an amphiphilic adjuvant.

8. Immunogen according to claim 5, comprising more than one type of antigens or antigenic determinants, which are characteristic of more than one type of pathogen against which immunization is desired.

9. Immunogen according to claim 5 that has been stabilized by having at least a portion of the antigenic determinants or antigens, or at least a portion of the amphiphilic adjuvant molecule, or a portion of each, linked to one another.

10. Immunogen according to claim 5, characterized in that it is encapsulated.

11. An immunogen according to claim 5, comprising at least one type of amphiphilic adjuvant selected from the group consisting of avridine (N,N-dioctadecyl-N',N'-bis(2-hydroxyethyl)-propanediamine); 4-aminomethyl-1-(2,3-(di-n-decyloxy)-n-propyl)-4-phenylpiperidine; dimethyl-dioctadecylammonium bromide; laurylmuramyl-dipeptide; lauryltetrapeptide (N²-[N-(N-lauryl-L-alanyl)-gamma-D-glutamyl]-N⁶-(glycyl)-D,D-L,L-2,6-diaminepimelamic acid; L-tyrosine and alkyl derivatives thereof.

12. An immunogen according to claim 5, comprising at least one type of amphiphilic adjuvant selected from the group consisting of maltose tetrapalmitate, pluronic polyols, L-tyrosineazobenzene-p-arsonate, sorbitanmonooleate, trehalose, retinoic acid, D,L-α-tocopherol, lipid A, a saponin, a carbomer and derivatives thereof.

13. Immunogen according to claim 6, characterized in that it contains saponins as amphiphilic adjuvants.

14. Immunogen according to claim 13, comprising more than one type of antigen or antigenic determinant characteristic of more than one type of pathogen against which immunization is desired.

15. Immunogen according to claim 13, that has been stabilized by having at least a portion of the antigenic determinant or determinant or antigen, or at least a portion of the amphiphilic adjuvant molecule, or a portion of each, linked to one another.

16. Immunogen according to claim 6, comprising more than one type of antigen or antigenic determinant characteristic of more than one type of pathogen against which immunization is desired.

17. Immunogen according to claim 16, that has been stabilized by having at least a portion of the antigenic determinant or antigen, or at least a portion of the amphiphilic adjuvant molecule, or a portion of each, linked to one another.

18. Immunogen according to claim 6, that has been stabilized by having at least a portion of the antigenic determinant or antigen, or at least a portion of the amphiphilic adjuvant molecule, or a portion of each, linked to one another.

19. Immunogen according to claim 6, which is encapsulated.

20. Immunogen according to claim 7, comprising more than one type of antigen or antigenic determinant characteristic of more than one type of pathogen against which immunization is desired.

21. Immunogen according to claim 20, that has been stabilized by having at least a portion of the antigenic determinant or antigen, or at least a portion of the amphiphilic adjuvant molecule, or a portion of each, linked to one another.

22. Immunogen according to claim 7 that has been stabilized by having at least a portion of the antigenic determinants that are characteristic of more than one type of pathogen against which immunization is desired.

23. Immunogen according to claim 7, characterized in that it is encapsulated.

24. Immunogen according to claim 8, that has been stabilized by having at least a portion of the antigenic determinant or antigen, or at least a portion of the amphiphilic adjuvant molecule, or a portion of each, linked to one another.

25. Immunogen according to claim 8, characterized in that it is encapsulated.

26. Pharmaceutical preparation having an immunizing action, comprising an effective amount of at least one immunogen as defined in claim 5.

27. Pharmaceutic preparation according to claim 26, comprising two or more different types of said immunogens.

28. Pharmaceutical preparation according to claim 26, comprising a plurality of said immunogens in a delayed-release dosage form.

29. Pharmaceutical preparation according to claim 28, characterized in that it contains an effective amount of two or more different types of the said immunogens.

30. Pharmaceutical preparation having an immunizing action, characterized in that it contains an effective amount of at least one immunogen as defined in claim 6.

31. Pharmaceutical preparation according to claim 30, characterized in that it contains two or more different types of the said immunogens.

32. Pharmaceutical preparation according to claim 30, characterized in that it contains a plurality of the said immunogens in a delayed-release dosage form.

33. Pharmaceutical preparation according to claim 32, characterized in that it contains two or more different types of the said immunogens.

34. Pharmaceutical preparation having an immunizing action, characterized in that it contains an effective amount of at least one immunogen as defined in claim 7.

35. Pharmaceutical preparation according to claim 34, characterized in that it contains two or more different types of the said immunogens.

36. Pharmaceutical preparation according to claim 34, characterized in that it contains a plurality of the said immunogens in a delayed-release dosage form.

37. Pharmaceutical preparation according to claim 36, characterized in that it contains two or more different types of the said immunogens.

38. Pharmaceutical preparation having an immunizing action, characterized in that it contains an effective amount of at least one immunogen as defined in claim 8.

39. Pharmaceutical preparation according to claim 38, characterized in that it contains two or more different types of the said immunogens.

40. Pharmaceutical preparation according to claim 38, characterized in that it contains a plurality of the said immunogens in a delayed-release dosage form.

41. Pharmaceutical preparation according to claim 40, characterized in that it contains two or more different types of the said immunogens.

42. Immunogen according to claim 9, characterized in that it is encapsulated.

43. Pharmaceutical preparation having an immunizing action, characterized in that it contains an effective amount of at least one immunogen as defined in claim 9.

44. Pharmaceutical preparation according to claim 43, characterized in that it contains two or more different types of the said immunogens.

45. Pharmaceutical preparation according to claim 43, characterized in that it contains a plurality of the said immunogens in a delayed-release dosage form.

46. Pharmaceutical preparation according to claim 45, characterized in that it contains two or more different types of the said immunogens.

47. Pharmaceutical preparation having an immunizing action, characterized in that it contains an effective amount of at least one immunogen as defined in claim 10.

48. Pharmaceutical preparation according to claim 47, characterized in that it contains two or more different types of the said immunogens.

49. Pharmaceutical preparation according to claim 47, characterized in that it contains a plurality of the said immunogens in a delayed-release dosage form.

50. Pharmaceutical preparation according to claim 49, characterized in that it contains two or more different types of the said immunogens.

* * * * *